(12) United States Patent
Beumer et al.

(10) Patent No.: US 11,851,404 B2
(45) Date of Patent: Dec. 26, 2023

(54) INTERMEDIATES FOR THE VITAMIN A SYNTHESIS

(71) Applicant: DSM IP ASSETS B.V., Heerlen (NL)

(72) Inventors: Raphael Beumer, Kaiseraugst (CH); Werner Bonrath, Kaiseraugst (CH); Marc-André Mueller, Kaiseraugst (CH); Bettina Wüestenberg, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 17/676,077

(22) Filed: Feb. 18, 2022

(65) Prior Publication Data

US 2022/0169590 A1 Jun. 2, 2022

Related U.S. Application Data

(63) Continuation of application No. 16/645,614, filed as application No. PCT/EP2018/074748 on Sep. 13, 2018, now abandoned.

(30) Foreign Application Priority Data

Sep. 22, 2017 (EP) .................................... 17192631

(51) Int. Cl.
| | |
|---|---|
| *C07C 67/293* | (2006.01) |
| *C07B 49/00* | (2006.01) |
| *C07C 403/08* | (2006.01) |
| *C07C 403/12* | (2006.01) |
| *C07C 69/145* | (2006.01) |

(52) U.S. Cl.
CPC ............ *C07C 67/293* (2013.01); *C07B 49/00* (2013.01); *C07C 403/08* (2013.01); *C07C 403/12* (2013.01); *C07C 69/145* (2013.01)

(58) Field of Classification Search
CPC ..... C07C 67/08; C07C 67/293; C07C 69/145; C07C 403/08; C07C 403/12; C07B 49/00; C07B 37/08

See application file for complete search history.

(56) References Cited

U.S. PATENT DOCUMENTS

| | | | | |
|---|---|---|---|---|
| 2,369,166 | A | * | 2/1945 | Milas .................... C07C 403/12 568/824 |
| 2,451,739 | A | | 10/1948 | Isler |
| 3,062,875 | A | | 11/1962 | Bain |
| 3,928,400 | A | | 12/1975 | Olson |

FOREIGN PATENT DOCUMENTS

GB 418723 * 10/1934

OTHER PUBLICATIONS

Overman, L.E. et al., Palladium (II)—Catalyzed rearrangement of allylic acetates, Tetrahedron Letters, No. 4, pp. 321-324 (Year: 1979).*
International Search Report for PCT/EP2018/074748, dated Nov. 29, 2018, 4 pages.
Written Opinion of the ISA for PCT/EP2018/074748, dated Nov. 29, 2018, 5 pages.
Overman et al., "*Palladium (II)—catalyzed rearrangement of allylic acetates*", Tetrahedron Letters No. 4, Jan. 1, 1979, pp. 321-324.
Fontán, Nolia et al, "Synthesis of $C_{40}$-Symmetrical Fully Conjugated Carotenoids by Olefin Metathesis," *Eur. J. Org. Chem.* 2011, 6704-6712.
Solladie, Guy et al, "Highly Stereoselective Synthesis of Vitamin A and All-Trans Retinoic Acid by Low-Valent Titanium Induced Reductive Elimination," Tetrahedron Letters, vol. 29, No. 2, pp. 213-216 (1988).
Iriye, Ryozo et al, "Formation of 4-Hydroxy-3,7-dimethyl-2,6-octadienal (5-Hydroyxcitral) from 3,7-Dimethyl-2,6-octadienal (Citral) and its Biological Activity against Sarcoma 180," *Agric. Biol. Chem.*, 48 (12), 2923-2925 (1984).
Van den Berg, Ellen M.M et al, "Synthesis of specifically deuteriated 9- and 13-demethylretinals," *Recl. Trav. Chim. Pays-Bas*, 109, 160-167 (1990).
Tutorskaya, O.O. et al, Synthetic Investigations in the Chemistry of Polyene Compounds LII.* Synthesis of Retinoic and Dihydroretinoic Esters by the Reformatskii Reaction, Journal of Organic Chemistry USSR (EN Translation), 1991, vol. 27(&.1), pp. 1237-1240.
Robeson, C.D. et al, "Synthesis of Geometric Isomers of Vitamin A," Journal of the American Chemical Society, 1955, vol. 77, pp. 4111-4117.
E.J. Corey et al, *New Methods for the Oxidation of Aldehydes to Carboxylic Acids and Esters*, Journal of the American Chemical Society, 90:20, 5616-5617, Sep. 25, 1968.
J.A. Pardoen et al, *Synthesis of retinals labelled at positions 14 and 15 (with $^{13}C$ and/or $^{2H}$)*, Receil. Journal of the Royal Netherlands Chemical Society, 103/4, 135-141, Apr. 1984.

* cited by examiner

*Primary Examiner* — Yate' K Cutliff
(74) *Attorney, Agent, or Firm* — NIXON & VANDERHYE P.C.

(57) ABSTRACT

Processes for synthesizing new compounds that may usefully be employed in organic synthesis, especially in the synthesis of vitamin A or β-carotene and derivatives thereof, e.g. canthaxanthin, astaxanthin or zeaxanthin are disclosed. The new compounds are especially useful as intermediates (building blocks) in the synthesis of vitamin A or β-carotene, preferably vitamin A.

11 Claims, No Drawings

INTERMEDIATES FOR THE VITAMIN A SYNTHESIS

This application is a continuation of U.S. patent application Ser. No. 16/645,614 filed on Mar. 9, 2020 (now abandoned), which in turn is the U.S. national phase of International Application No. PCT/EP2018/074748 filed Sep. 13, 2018, which designated the U.S. and claims priority to European Patent Application No. 17192631.4 filed Sep. 22, 2017 the entire contents of each of which are hereby incorporated by reference.

The present invention relates to new compounds, to their synthesis and their use in organic synthesis, especially in the synthesis of vitamin A, Vitamin A acetate, or β-carotene and derivatives thereof, e.g. canthaxanthin, astaxanthin or zeaxanthin.

Especially to be mentioned is that the new compounds are useful as intermediates (building blocks) in the synthesis of vitamin A or β-carotene, preferably in the synthesis of vitamin A (or vitamin A acetate).

Vitamin A or its derivatives such as Vitamin acetate

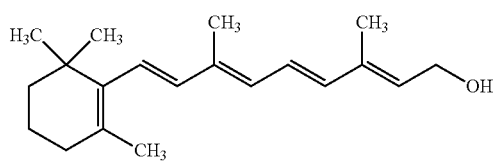

(all-E)-retinol (vitamin A)

is an important ingredient for many applications. Vitamin A plays a role in a variety of functions throughout the (human) body, such as e.g. vision process, gene transcription, immune function, bone metabolism, haematopoiesis, skin and cellular health and antioxidant function.

Due to the importance of vitamin A (and its derivatives) and the complexity of the synthesis thereof, there is always a need for improved processes of production.

The goal of the present invention was to find easily accessible compounds, which can then be used in an improved synthesis of vitamin A or its derivates, or β-carotene, preferably vitamin A (acetate).

The aim was achieved by the compounds and the synthesis as disclosed and described below.

Three new compounds, which are useful intermediates, have been found:

β-Cyclogeranylgeranyl acetate (compound of formula (I))

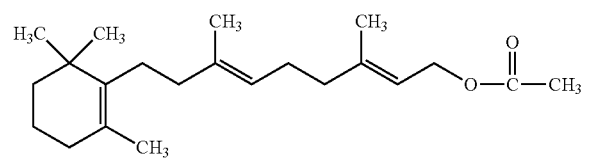

as well as β-cyclogeranyllinalyl acetate (compound of formula (II))

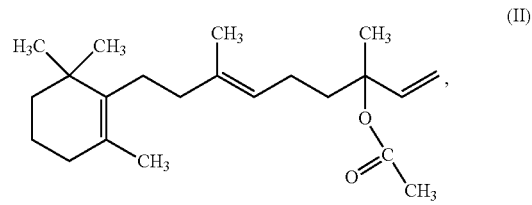 [SMILES: C=CC(C)(CC/C=C(\C)CCC1=C(C)CCCC1(C)C)OC(C)=O]

which is a precursor compound for the compound of formula (I).

Therefore, an embodiment of the present invention is the compound of formula (I)

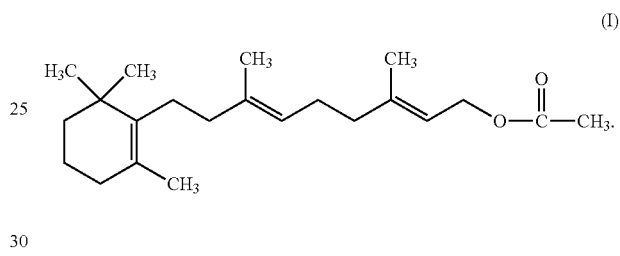

Therefore, another embodiment of the present invention is the compound of formula (II)

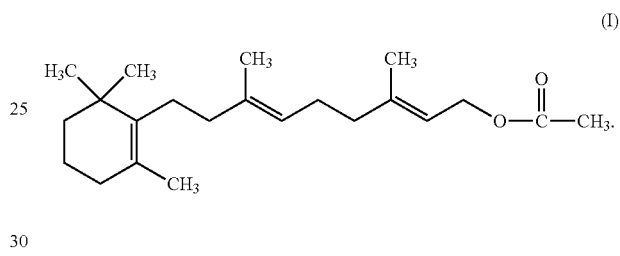

The new synthesis uses 6-methyl-8-(2,6,6-trimethyl-1-cyclohexen-1-yl)-5-octen-2-one (compound of formula (III))

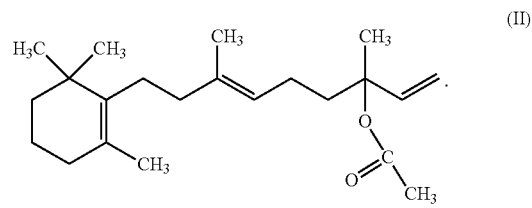 [SMILES: C=CC(C)(CC/C=C(\C)CCC1=C(C)CCCC1(C)C)OC(C)=O]

as a starting material.

6-Methyl-8-(2,6,6-trimethyl-1-cyclohexen-1-yl)-5-octen-2-one (compound of formula (III)) was synthesized according to literature-known procedures, such as e.g. the following way

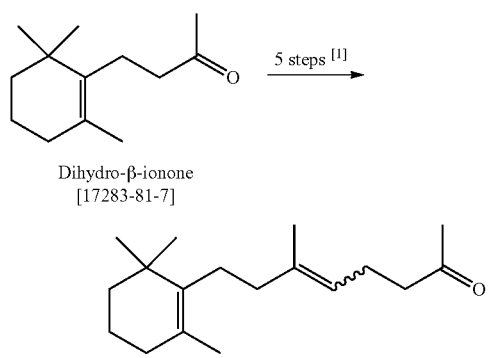

Dihydro-β-ionone
[17283-81-7]

[1] L. Ruzicka, W. Fischer, Helv. Chim. Acta 1934, 17, 633-639.

6-Methyl-8-(2,6,6-trimethyl-1-cyclohexen-1-yl)-5-octen-2-one can be converted into β-cyclogeranyllinalool (compound of formula (IV)) by standard organic chemistry methods, e.g. by Grignard reaction.

The reaction scheme of the production of the compounds of formula (I) and (II) is the following:

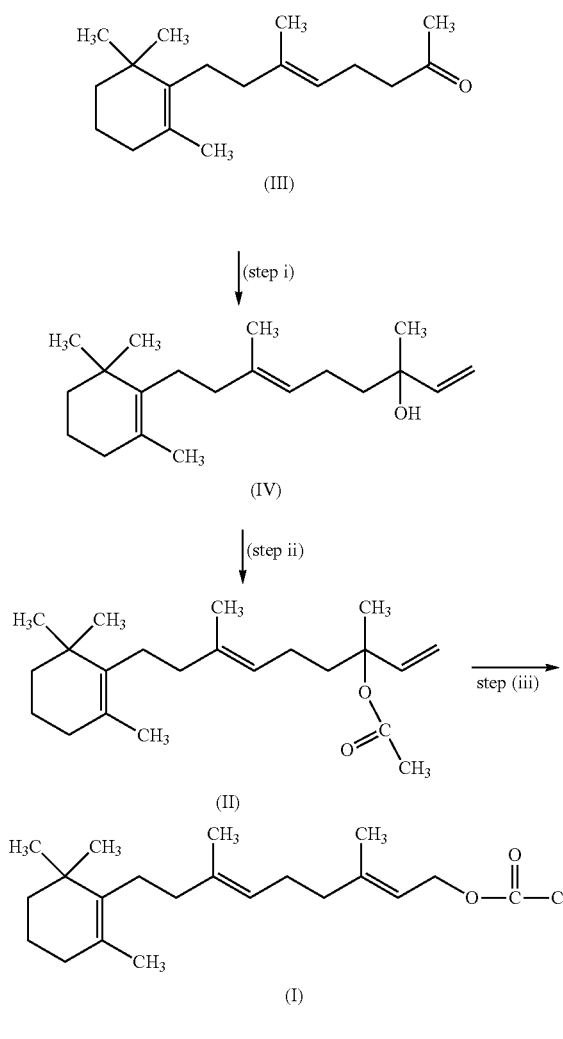

Therefore, the present invention relates to a process to produce the compound of formula (II)

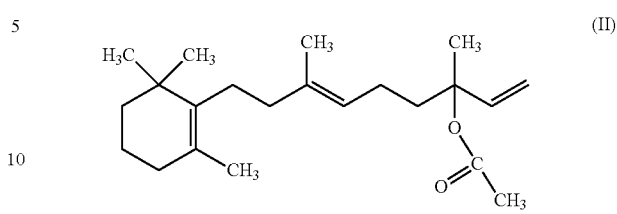

wherein the compound of formula (IV)

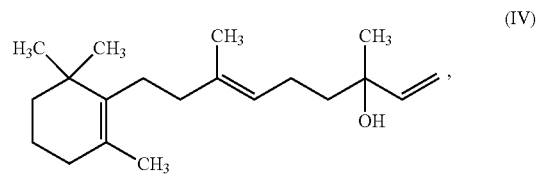 [SMILES: C=CC(C)(O)CC/C=C(\C)CCC1=C(C)CCCC1(C)C]

is reacted with a compound (acetic acid anhydride or similar) to form the compound of formula (II).

Step (i)

Step (i) can be carried out according to standard organic chemistry methods, e.g. Grignard reaction.

Step (ii)

The compound of formula (IV) is acetylated. That can be done by commonly known compounds, such as for example acetic acid anhydride.

The reaction of step (ii) is carried out in presence of an tertiary amine, preferred triethylamine. It is very common and preferred that also at least one nucleophilic catalyst is used, such as for example dimethyl aminopyridine.

Usually the reaction of step (ii) is carried out under an inert gas atmosphere.

The reaction of step (ii) is usually carried out at elevated temperatures, usually above 30° C., (in the range of 30-80° C.).

The product which is then obtained (compound of formula (II)) can be isolated and if needed further purified. The yields, which are obtained are usually above 80%.

Step (iii)

Compound of formula (I) is obtained by the reaction of the compound of formula (II). It is a rearrangement reaction. (step (iii)).

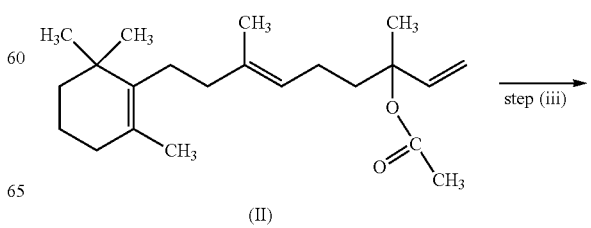

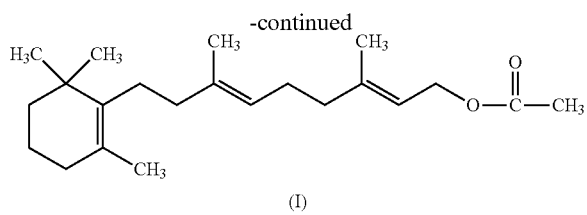

(I)

Usually the reaction of step (iii) is carried out in an organic solvent. Suitable solvents are ethers, e.g. THF, toluene, methyl-THF, methyl cyclopentyl ether, tert.-butyl methyl ether, tert.-butyl ethyl ether, tert.-amyl methyl ether or mixtures thereof. Most preferred solvents are are ethers, such as THF or 2-MeTHF.

Usually the reaction of step (iii) is carried out in the presence of a catalyst such bis(acetonitrile)-dichloropalladium or bis(benzonitrile)-dichloropalladium.

The product is then isolated and usually purified by commonly known methods. The compound of formula (I) is usually obtained in an overall yield (based on the compound of formula (II)) of more than 50%.

The compounds of formula (I) and (II) according to the present invention can be used in organic synthesis.

Preferably the new compounds are useful as intermediates (building blocks) in the synthesis of vitamin A or β-carotene or derivatives thereof, preferably vitamin A. Therefore, a further embodiment of the present invention relates to the use of compounds of formula (I) and (II) in organic synthesis. A preferred embodiment of the present invention relates to the use of compounds of formula (I) and (II) as intermediates (building blocks) in the synthesis of vitamin A or β-carotene, preferably vitamin A.

The following examples serve to illustrate the invention. The temperature is given in ° C. and all percentages are related to the weight.

EXAMPLES

Example 1: Synthesis of β-cyclogeranyllinalool

Under inert gas atmosphere, 22 mmol of (E)-6-methyl-8-(2,6,6-trimethylcyclohex-1-en-1-yl)oct-5-en-2-one (III) were dissolved in 22 ml of anhydrous THF. The solution was cooled to 0-5° C. with an ice-bath. Over 2 hours, 33 mmol vinyl magnesium bromide solution (1 M in THF) were added dropwise so that the temperature remains between 0-5° C. After complete addition, stirring was continued for 1 hour. After that the ice-bath was removed and the reaction was warmed to room temperature. After 1 hour at 24° C., sat. NH$_4$Cl-solution (30 ml) was added dropwise over 10 min (exothermic). After stirring for another 30 min the mixture was diluted with methylene chloride (100 ml) and washed with brine (2×45 ml). The aqueous layers were re-extracted with methylene chloride (2×100 ml). The combined organic layers were dried over sodium sulfate, filtered and concentrated under reduced pressure. The crude product was purified by column chromatopgraphy (SiO$_2$, cyclohexane/diisopropyl ether 8:2).

Example 2: Synthesis of β-cyclogeranyllinalool acetate

Under inert gas atmosphere, 3.44 mmol β-cyclogeranyllinalool were dissolved in 6.9 ml of toluene. At room temperature, 8.61 mmol of triethylamine and 1.722 mmol of dimethyl aminopyridine (DMAP) were added. To the colorless solution were added 8.61 mmol of acetic acid anhydride. Then the reaction mixture was warmed to 50° C. and stirred for 2 hours.

The reaction mixture was cooled to room temperature, transferred into a separation funnel and diluted with 15 ml of diethyl ether. The organic layer was subsequently washed with semi-saturated NaHCO$_3$ solution (30 ml), water (30 ml) and brine (30 ml). The aqueous layers were re-extracted with diethyl ether (30 ml). The combined organic layers were dried over Na$_2$SO$_4$, filtered and concentrated under reduced pressure. The crude product was purified by column chromatography (SiO$_2$, cyclohexane/diisopropyl ether 8:2). The purified product was obtained as colorless liquid in 81% yield.

Example 3: Synthesis of β-cyclogeranylgeraniol acetate

Under inert gas atmosphere, 0.05 mmol bis(acetonitrile)-dichloropalladium were dissolved in 1 ml of anhydrous THF. At room temperature, a solution of 1 mmol of β-cyclogeranyllinalool acetate in 4 ml of anhydrous THF was added within 20 min. After stirring for 4 hours at room temperature, the reaction was complete. The solvent was removed and the crude product was purified by column chromatography (SiO$_2$, n-hexane/ethyl acetate 95:5). The purified product was obtained as yellow liquid in 50% yield.

The invention claimed is:
1. A process for producing a compound of formula (I),

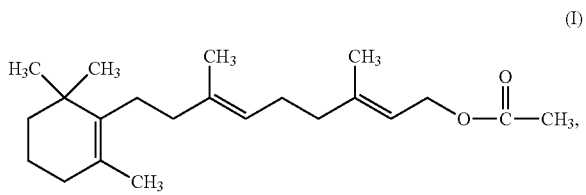 [SMILES: CC(=O)OC/C=C(\C)CC/C=C(\C)CCC1=C(C)CCCC1(C)C]

(I)

wherein the process comprises the sequential steps of:
(i) subjecting a compound of formula (III):

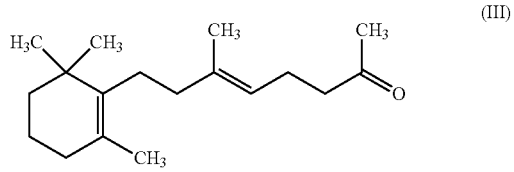 [SMILES: CC(=O)CC/C=C(\C)CCC1=C(C)CCCC1(C)C]

(III)

to Grignard reaction conditions to form a compound of formula (IV):

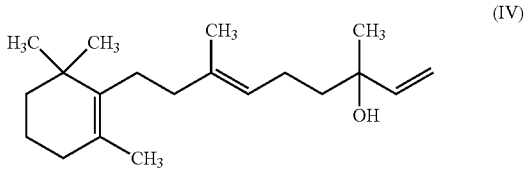 [SMILES: C=CC(C)(O)CC/C=C(\C)CCC1=C(C)CCCC1(C)C]

(IV)

(ii) acetylating the compound of formula (IV) to form a compound of formula (II):

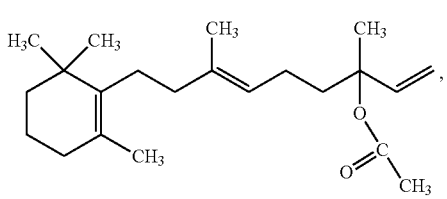

and thereafter (iii) subjecting the compound of formula (II) to rearrangement conditions in the presence of an organic solvent to obtain the compound of formula (I).

2. The process according to claim 1, wherein step (ii) is conducted under an inert gas atmosphere.

3. The process according to claim 1, wherein step (ii) is carried out at an elevated temperature above 30° C.

4. The process according to claim 3, wherein the elevated temperature is in a range of 30° C. to 80° C.

5. The process according to claim 1, wherein step (ii) is carried out in the presence of a tertiary amine.

6. The process according to claim 5, wherein the tertiary amine comprises trimethylamine.

7. The process according to claim 1, wherein step (ii) is carried out in the presence of at least one nucleophilic catalyst.

8. The process according to claim 7, wherein the at least one nucleophilic catalyst comprises dimethyl aminopyridine.

9. The process according to claim 1, wherein the organic solvent of step (iii) is selected from the group consisting of tetrahydrofuran (THF), toluene, methyl-tetrahydrofuran, methyl cyclopentyl ether, tert-butyl methyl ether, tert-butyl ethyl ether, tert-amyl methyl ether and mixtures thereof.

10. The process according to claim 1, wherein step (iii) is carried out in the presence of bis(acetonitrile)-dichloropalladium or bis(benzonitrile)-dichloropalladium as catalyst.

11. The process according to claim 1, wherein step (iii) is practiced to obtain a yield of the compound of formula (I), based on the compound of formula (II), which is more than 50%.

* * * * *